United States Patent [19]
Beyer et al.

[11] Patent Number: 5,741,505
[45] Date of Patent: Apr. 21, 1998

[54] EDIBLE PRODUCTS HAVING INORGANIC COATINGS

[75] Inventors: Daniel L. Beyer; Theodore E. Jach, both of Netcong, N.J.; Dennis L. Zak, Doylestown, Pa.; Ralph A. Jerome, Blairstown, N.J.; Frank P. DeBrincat, Tobyhanna, Pa.

[73] Assignee: Mars, Incorporated, McLean, Va.

[21] Appl. No.: 376,029

[22] Filed: Jan. 20, 1995

[51] Int. Cl.$^6$ .................................................. A61K 47/00
[52] U.S. Cl. .................... 424/439; 424/474; 426/94; 426/97; 426/98; 426/138; 426/284; 426/292; 426/322; 426/654
[58] Field of Search ........................... 424/464, 474, 424/439; 426/94, 93, 96, 97, 98, 89, 138–140, 282, 284, 289, 292, 322, 654

[56] References Cited

U.S. PATENT DOCUMENTS

| | | | |
|---|---|---|---|
| 2,093,260 | 9/1937 | Wilder et al. | 99/80 |
| 2,970,056 | 1/1961 | Benson et al. | 426/96 |
| 4,196,219 | 4/1980 | Shaw et al. | 426/89 |
| 4,220,667 | 9/1980 | Jakinovich, Jr. | 426/96 |
| 4,233,324 | 11/1980 | Jehle et al. | 426/96 |
| 4,268,411 | 5/1981 | Iwata et al. | 252/316 |
| 4,278,695 | 7/1981 | Velasco | 426/289 |
| 4,288,460 | 9/1981 | Ciliberto et al. | 426/96 |
| 4,504,502 | 3/1985 | Earle et al. | 426/293 |
| 4,664,920 | 5/1987 | Saleeb | 426/74 |
| 4,707,365 | 11/1987 | Haynes et al. | 426/94 |
| 4,720,378 | 1/1988 | Forse et al. | 426/89 |
| 4,786,511 | 11/1988 | Huzinec et al. | 426/5 |
| 4,802,924 | 2/1989 | Woznicki et al. | 427/3 |
| 4,824,681 | 4/1989 | Schobel et al. | 426/5 |
| 4,832,967 | 5/1989 | Autant et al. | 426/96 |
| 4,888,199 | 12/1989 | Felts et al. | 427/10 |
| 4,988,521 | 1/1991 | Fan | 426/93 |
| 5,077,053 | 12/1991 | Kuncewitch et al. | 424/441 |
| 5,094,862 | 3/1992 | Bunick et al. | 426/96 |
| 5,098,723 | 3/1992 | DuBois et al. | 426/96 |
| 5,286,502 | 2/1994 | Meyers | 426/5 |
| 5,298,273 | 3/1994 | Ito | 426/549 |
| 5,328,705 | 7/1994 | Wilhoit et al. | 426/113 |

FOREIGN PATENT DOCUMENTS 43-71016507  6/1968  Japan.

OTHER PUBLICATIONS

J.J. Kester and O.R. Fennema, "Edible Films and Coatings: A Review", *Food Technology*, pp. 49–59 (Dec. , 1986).

Ratner et al., "Plasma Deposition and Treatment for Biomaterial Applications", *Plasma Deposition, Treatment and Etching of Polymers*, Academic Press, San Diego, pp. 465–515 (1990).

Greener and Fennema, "Evaluation of Edible, Bilayer Films for Use as Moisture Barriers for Food", *Journal of Food Science*, vol. 54, No. 6, pp. 1400–1406 (1989).

Kester and Fennema, "An Edible Film of Lipids . . . ", *Journal of Food Science*, vol. 54, No. 6, pp. 1383–1389 (1989).

Gontard et al., "Edible Composite Films of Wheat Gluten . . . ", *International Journal of Food Science and Technology*, (1994) vol. 29, pp. 39–50.

Gölaner et al., "RF-Plasma-Modified Polystyrene Surfaces for Studying Complement Activation", *J. Biomater Sci. Polymer Edn.*, vol. 4, No. 1 pp. 25–30 (1992).

(List continued on next page.)

*Primary Examiner*—James J. Seidleck
*Assistant Examiner*—Michael A. Williamson
*Attorney, Agent, or Firm*—Leonard J. Santisi

[57] ABSTRACT

An edible product having a thin inorganic coating on at least a portion of its surface. The coating preferably forms a moisture/oxygen barrier to result in a coated edible product having an improved shelf-life. The edible products include foods and pharmaceuticals. The inorganic materials used for the coating include $SiO_2$, SiO, MgO, CaO, $TiO_2$, ZnO and MnO. Processes and apparatuses for depositing a thin film of inorganic material onto an edible substrate are also disclosed. The preferred processes include sputtering and vapor deposition. The preferred apparatus provides for the continuous production of coated edible products.

29 Claims, 3 Drawing Sheets

OTHER PUBLICATIONS

Desu et al., "Low Temperature CVD of $SiO_2$ Films Using Novel Precursors", *J. Electrochem. Soc.*, vol. 139, No. 9, (1992).

Tedder et al., "Mechanistic Studies of Dielectric Thin Film Growth . . . ", *J. Appl. Phys.* vol. 69(10), pp. 7037–7049 (1991).

Brody, "Glass–Coated Flexible Films for Packaging: An Overview", *Packaging Technology & Engineering*, pp. 44–47 (1994).

"2nd Place: QLF Barrier Coating", *Packaging Technology and Engineering*, (Dec. 1993/Jan. 1994), p. 19.

"ECD: Silica Barrier–Coating Technology", 1994 *Trade Show Print*.

EDIBLE PRODUCTS HAVING INORGANIC COATINGS

BACKGROUND OF THE INVENTION

1. Field of the Invention

This invention relates to edible products, such as a food or a pharmaceutical composition, which are coated with edible inorganic films. The invention also relates to a method of producing an edible product having an inorganic coating, and an apparatus for processing edible products coated with an inorganic film.

The invention also relates to reducing food packaging waste and disposal problems as the outer package material requirements may be reduced if the edible product itself is more shelf-stable.

Moreover, the invention also allows for the creation of new food products and low fat products that require the use of moisture which heretofore would have had a negative impact on shelf-life.

2. Description of the Prior Art

In many conventional food products, moisture, oxygen, or fat migrates to soften, oxidize or bloom the products, limiting the product's shelf-life. "Shelf-life" is the time that elapses before stored foods become unsuitable for use due to degradation. The migration of moisture, oxygen or other components in foods can cause deleterious changes in the taste, texture, smell, nutritive value, storage stability and saleabilty of products. "Texture" is the structure, feel, and appearance of a product, including the nature and arrangement of the constituent particles on a substance. The transfer of moisture can occur between a food and its environment and/or within different components of a nonhomogeneous food system. For example, deterioration of the texture of dry bakery materials, such as the crust of a filled pie, occurs when moisture is transferred from the high-moisture filling to the crust. At the same time, the filling changes because of loss of moisture to the crust or atmosphere, resulting in a gummy or sticky consistency.

U.S. Pat. No. 4,707,365 to Haynes et al. discloses that chocolate chips used in cookies lose chocolate flavor impact on aging. This loss of flavor has been found to be due to the higher water activity of the cookie crumb relative to the much lower water activity in the chocolate chips. Specifically, the moisture in the cookie crumb diffuses into the chocolate chips and desorbs the chocolate flavor compounds present therein. These desorbed compounds then diffuse back into the cookie crumbs. The result is chocolate chip cookies which have less chocolate flavor impact over time. The present invention would overcome this problem by providing a moisture barrier coating on the surface of the chocolate chips to prevent the migration of moisture.

Similarly, problems exist when candy coated confections are added instead of, or in conjunction with, chocolate chips to cookies or ice cream products. It has been found that over time the coloring of the candy coating often runs, causing discoloring of the cookie or ice cream. The present invention would overcome this problem by providing a barrier on the candy coating to prevent it from running.

Edible films are of tremendous importance because of the impact they have on obviating the problems noted above and on extending the shelf-life of foods. Edible films also expand the opportunities for new foods and increase the consumer expectation for a variety of fresh foods by reducing the requirements for antioxidants and preservatives. There also is a benefit in expanding distribution channels due to extended shelf-life for foods. In addition, the edible films reduce the amount of packaging required to preserve the edible product since the film acts as a barrier to moisture and/or oxygen and improves the shelf-life. By reducing packaging needs, the edible films have a beneficial effect on environmental regulations and concerns.

The use of edible barriers on food products to minimize the deleterious effects described above is known in the art. However, thus far, the development of edible water and oxygen barriers has focused upon barriers containing organic materials, particularly lipids and proteins. The development of water vapor barriers has centered upon barriers containing primarily cellulose, lipid and protein. In general, barriers containing lipid are less permeable to water vapor than barriers containing proteins. However, protein containing barriers are not practical for certain products, for example fruits.

A non-lipid support is required to reduce the brittleness/fragility associated with barriers containing lipids. Cellulose films are commonly used as a support film. Plasticizers are then added to reduce the brittleness. Proteins can be used in both the support film and the barrier, but these are often not as effective as a lipid barrier.

Recent work has been concentrated on protein and carbohydrate films. Proteins such as collagen, zein, gelatin, gluten and various milk proteins have been the focus of much recent work. Carbohydrates such as chitosan, modified cellulose, and methyl cellulose are also being studied. These materials are useful in many food areas where water activity must be maintained to retain the product's quality and microbial safety. More research is needed before these technologies will become more widely accepted.

The underlying problem with prior art edible films is the large quantities required for the barrier to be effective. The effective quantity is directly related to the coating thickness. With a thicker barrier there is poor consumer acceptance because a thicker barrier affects the mouth feel quality due to textural differences. In general, the more effective coatings have poorer mouth feel quality. An example of this phenomenon would be a wax film barrier. Wax is an effective barrier, but with a wax barrier it's necessary to add an amount such that it becomes tough in the mouth and does not melt (i.e. paraffin wax). Fruits are sometimes provided with wax layers to increase shelf-life but these wax layers are detectable by consumers and are thus undesirable. These waxes, however, decrease moisture loss by a half.

Shellacs are effective moisture barriers, and are water or solvent disperseable. While solvents are the most effective dispersant for shellacs they are undesirable as solvent flavor is absorbed into the food.

There are no known edible products that utilize the insoluble inorganic films that are disclosed by this invention. Other water based barriers have only a fraction of the effectiveness in comparison with the presently disclosed insoluble inorganic coatings, for example a $SiO_2$ coating. The food industry has thus far mostly used fat, gums or proteins as barriers. The primary limitation of these prior art coatings are the large quantity required to be effective, thus altering the taste and mouth-feel of the product. In some cases crystallizing proteins or starches on the surface will improve the moisture barrier for the food. In most cases those components are soluble in water.

Therefore, ideally, the optimal barrier would be an ultra thin non-toxic layer which is not perceived in the mouth, and insoluble in water. Such a barrier would prevent oxygen and moisture migration for long periods of time.

The following references and those referred to hereinafter, each of which are hereby incorporated by reference, disclose the state of the art.

U.S. Pat. No. 2,093,260 to Wilder et al. discloses the detrimental effect salt has in fat containing ready-to-eat cereal foods. When salt is used in the common manner of making these foods, its presence results in appreciable amounts of free hydrochloric acid. The patent discloses a process whereby salt flavor may be obtained without jeopardizing the keeping qualities of food having a substantial fat content by avoiding the addition of the salt to the food until after the completion of the high-temperature operation which results in the decomposition of the fat within the food. (Column 2, lines 49–56). After the high temperature toasting operation, the foods are coated with a salt solution and dried to obtain a food product having the essential salt flavoring without its detrimental effects.

U.S. Pat. No. 4,196,219 to Shaw et al. discloses a method of extending the storage life of frozen cooked foods, such as meats, poultry and fish. The method comprises the steps of cooking the food, coating the cooked food with an edible coating having a composition comprising the calcium salt of carrageenan, freezing the food coated with the calcium salt of carrageenan, and storing the coated food in the frozen state. The coating is applied in a substantially uniformly thick coating on the food.

U.S. Pat. No. 4,288,460 to Ciliberto et al. discloses granular water-soluble food ingredients, which deteriorate upon exposure to the atmosphere, that are protected by encapsulation in a protective coating containing a fatty acid derivative and a flow agent, i.e. fumed silica or carboxymethylcellulose. The resulting coated particles have an improved shelf life and still are substantially instantaneously soluble in water.

U.S. Pat. No. 4,504,502 to Roland et al. discloses a coated food product formed by applying an aqueous dispersion containing water soluble algin to the surface of a food substrate. The aqueous dispersion has a viscosity effective to substantially uniformly coat the surface of the food substrate. A dry gelling mixture is then applied to the algin coated food substrate for a period of time sufficient to form a substantially continuous edible alginate film along the surface of the food substrate. The film is sufficient to effectively retard the migration of moisture from the surface of the food substrate thereby retarding dehydration. The film also forms an oxygen barrier for retarding oxidation of the food substrate and retaining flavor within said food substrate.

U.S. Pat. No. 4,802,924 to Woznicki et al. discloses a method of coating pharmaceutical tablets, foods, confectionery forms and the like with polydextrose or a combination of polydextrose and cellulosic polymer, or a layer of polydextrose overcoated with a layer of cellulosic polymer.

U.S. Pat. No. 5,286,502 to Meyers et al. discloses a method of prolonging the shelf-life of sticks of chewing gum by coating both sides with an aqueous solution of an edible film forming agent, preferably a cellulose derivative, which, when partially dried, serves as an adhesive. A layer of wax is then applied to each of the layers of edible film forming agent.

U.S. Pat. No. 5,298,273 to Ito discloses edible containers suitable for frozen confections (e.g., ice cream, frozen yogurt and the like) and other food products made by initially baking a dough. The method involves sandwiching a farinaceous batter mixture containing sugar, oil and flour between a pair of heated platens and then heating and baking the batter mixture to effect alphatization of the starch and to evaporate moisture. Thus, after the initial baking, a de-watered edible sheet of baked batter will result. The de-watered edible sheet of baked batter is then re-moisturized (e.g., by spraying), molded to form a container and baked to form a crispy container for frozen confections and other food products.

OBJECTS OF THE INVENTION

It is an object of the present invention to provide a food product having an edible film coating which results in an extended shelf-life for the food product.

It is a further object of the present invention to provide a method for producing an edible product coated with an edible film.

It is still another object of the invention to provide a pre-made sheet of edible material which can be formed and subsequently applied as a coating onto an edible product.

SUMMARY OF THE INVENTION

The present invention relates to an edible film which overcomes the textural problems associated with coating edible products by using a continuous inorganic composition as a barrier layer. It is desirable to produce a layer that is very thin (0.05 micron or less) and amorphous to prevent cracking of the barrier if the product is flexed. The inorganic substance is preferably insoluble.

The main objective of the invention includes improving the shelf-life of food products and/or the flavor impact of food products. The present invention offers several advantages in comparison to current moisture barrier technology. The primary advantage is to increase the shelf-life of food products without effecting the taste and texture. The advantages also include the ability to develop new products with dual textures like crunchy jelly filled confections that would not become soft since the film would form a barrier between the jelly portion and the crunchy portion. Further, the advantages include the reduction of packaging used to protect food products, thereby reducing cost and environmental waste. Moreover, all these advantages are achieved without greatly effecting the look, taste, scent or feel of the edible product.

General Approach

The application of an inorganic film onto an edible product may be performed by a number of methods.

In one preferred method, the product is placed in a batch or continuous system that can produce a plasma. The system can be a simple corona discharge or as complex as a chemical plasma deposition. In any system, a higher success rate is achieved with a drier, more heat resistant, smoother, lower fat and higher density product.

The method preferably is one which enables the formation of a thin inorganic film inexpensively and quickly. A preferred embodiment of the invention includes a process in which the coating step is one of a series of steps in the continuous production of edible products.

The resultant coating covers the edible product to the extent necessary to improve shelf-life by maintaining water activity or retaining flavor. This may result in a coating on the entire product or a portion of the heterogenous product. For example, a pizza dough that has been baked is coated on one surface so that the high moisture sauce subsequently applied will not effect the baked dough, thereby improving the shelf-life of the product. The invention also allows for differently flavored foods (i.e. crackers) being packed within the same package without detrimental mixing of the flavors.

In some embodiments, there is a barrier to moisture transfer, but not a barrier to the transmission of oxygen, or vice versa. Lowering the oxygen permeability of food products decreases lipid oxidation, nonenzymatic browning and microbial growth. For example, if the edible product is high in polyunsaturated fat, a barrier extremely resistant to oxygen permeability is desired. Conversely, if the edible product is fresh fruits or vegetables, maintaining a proper balance of respiration is necessary to avoid anaerobic respiration which decreases the consumer acceptance of the product. Accordingly, the inorganic barrier selected has the desired character to result in a coated edible product having the desired properties.

The edible inorganic film is substantially continuous over at least a portion of, or over the, entire food product. The edible film is also thin (0.0001 to 0.5 microns) so that the product feel, look, and taste are not adversely affected. The edible film is advantageously thin enough, and the amount of inorganic material on the food product is advantageously small enough, so that the resultant coated edible product is within the standards and regulations (such as those published in Section 21 of the Code of Federal Regulations) for edible products.

Coating Systems

The coating systems that may be used to coat an inorganic material on the surface of edible products include: (1) sputtering or analogous thermal sublimation; (2) electron beam; and (3) plasma deposition. The level of development of the technology relating to the coating of inorganic materials has been intense in recent years. Both the biomedical and electronics fields have been involved in the technology because inorganic films have great utility in these areas as well.

Since high heat and/or low vacuums are often needed to make a plasma, care must be taken to avoid changing the products' composition or texture, for example, evaporation of moisture on the surface which is being coated. Lower vacuum processes are preferable if done at ambient or low temperature. Drier foods have shown a higher success rate as evaporation at the surface of the food is minimal if the food has a low moisture content. In certain applications, depending on the type of food product, it is also possible to freeze the food product to prevent evaporation.

Sputtering or analogous thermal sublimation systems take a target composition and bombard it with ions which have been accelerated towards the target by high radio frequencies or direct current potential. The momentum of the impacting ions transfers energy to the surface atoms of the target causing them to be ejected at high velocities onto the substrate to be coated.

An electron beam process imparts ample energy to sublime the substrate in a vacuum. However, the sublimation temperatures are generally too high for some edible products and the energy levels of the e-beam are ~20–40 kilowatts per gun and require nuclear shielding. While an electron beam process may be utilized it is more expensive, making it less attractive for food industry applications.

Plasma enhanced chemical vapor deposition is activated by means of electromagnetic energy which must be sufficient so that the gas or liquid separates into electrons, ions, and free radicals and other excited state species. "Plasma" is an ionized gas which contains substantially equal numbers of ions and electrons. The precursor compound is vaporized and introduced into a vacuum chamber where it is subjected to an electronic discharge. The electromagnetic field causes electrons to be ejected, creating ions and initiating a chain reaction to generate more charged particles. The excited species of gas in the glowing plasma is attracted to the surface of the food where the excited and neutral species of the compound are deposited on the substrate surface and built up atom by atom until a continuous layer is formed.

Microwave plasma enhanced chemical vapor deposition uses microwave energy in addition to the above process. This creates a similar product as described above.

The frequencies typically used in chemical plasma depositions range from about 10 KHz to about 1 GHz, preferably 10 KHz to 100 MHz, and pressures vary from about 0.00001 to about 50 torr. The power coupling can be capacitive, inductive or microwave.

While any of the above described coating processes may be employed the preferred method of coating the edible product is by chemical plasma deposition (CPD) if the products are required to be very uniform. Sputtering is the preferred method when high degrees of control are not needed, but rather less expensive production costs are important. The main advantage with CPD is that the process can be performed at lower vacuums and temperatures than sputtering. The main advantage of sputtering is that it reduces the possibility of side reactions which can form contaminates in the coating. Both sputtering and CPD are processes that have been improved and developed over the last 15 years by the electronic and biomedical fields. Also, CPD films have now been approved by the FDA for the flexible packaging on food contact surfaces.

In chemical plasma deposition a thin film depositing plasma is formed in a chamber by introducing at least one gaseous precursor into a region having a controlled electrical field. The process parameters that are usually controlled include the internal pressure level, the electrical field characteristics, the composition of the gas and its flow rate into the plasma. Varying these parameters will vary the characteristics and properties of the resultant film. It is, of course, desirable to control these plasma variables to produce a film coating having the desired film properties. As applied to the present invention, it is necessary to adjust the parameter to result in a film coating being substantially continuous, as well as having a uniform thickness and composition.

One method, disclosed by Felt et al. in U.S. Pat. No. 4,888,199, involves a process of depositing a thin film onto a surface of a substrate with the use of a plasma, wherein the plasma optical emission is monitored, analyzed and the results used to automatically control the nature of the plasma in order to control the characteristics of the deposited thin film.

The Edible Substrate Material

"Edible product" refers to either a food product or a pharmaceutical which can be consumed by humans or nonhumans (i.e., pets). The edible product can also include foods that are to be used only for display. The properties of the edible product to be coated, such as its surface smoothness, moisture content, heat resistance, fat content and density play an important consideration in the selection of the types of edible substrate material and its method of application. Optimal results are achieved when the food surface is smooth and dry. With a smoother surface a thinner coating has been found to be effective. The surface moisture of the product is also an important consideration since it is more difficult to coat a surface which is evaporating. More heat resistant products enable the use of lower pressure or vacuum processes and higher process temperatures to maintain the plasma which lower manufacturing costs. Higher fat products are non-polar making it more difficult for the coating to adhere to the surface. The surface will change due to the polymorphic nature of fats. Fats will change crystalline structures over time to achieve its lowest thermodynamic state. The polymorphic changes are generally to larger crystal sizes. This polymorphic expansion may cause cracking or irregularities in the coating. These problems are overcome by using edible products having a surface with a low fat content.

Also higher density products react better in a vacuum process because they will not expand. Products that expand could develop cracks in the coating and decrease the edible film's effectiveness. Freezing the products before the process may decrease many of these problems. However, since coatings formed by sputtering and CPD are amorphous and therefore inherently flexible, the problem of cracks caused by substrate expansion is not significant.

In another embodiment of the invention a precoating edible barrier is applied which covers some of the voids in the edible product, resulting in a smoother surface. This product is then coated with an inorganic layer. Such a process is beneficial in edible products where an enzyme or acid/base reaction could degrade the precoating. When that occurs the inorganic layer for barrier protection remains. This process is commercially important as it avoids the associated problems and expense of producing a plasma deposition at the food manufacturing plant.

Examples of some of the possible existing types of edible products that may be coated according to the present invention include:

Low moisture foods that need expensive barrier protection to prevent them from being soggy.

Hard candy that becomes sticky when exposed to high humidities.

Cookies and potato chips that also become soggy or stale when the bag is opened or stored for long periods of time and lose their crunch.

Food products that are for display, thereby requiring long shelf-lives. These products discolor and crack with time due to moisture loss.

Sugar coated confections/pharmaceuticals to prevent the color coating from rubbing off on the hands. Air and humidity solubilizes the coating sugars that carry the coloring.

Ready to eat cereals that when served in milk become soggy with time.

Cookies with jelly topping of chocolate chips which become soggy or lose chocolate flavor over time, thereby reducing shelf-life or taste.

Low fat systems which generally reduce fat by adding water, and which dry out over time limiting shelf-life.

The present invention enables the creation of otherwise impractical low fat/high moisture products by forming a moisture barrier film on high moisture foods to prevent the dehydration of the product. Accordingly, high moisture foods, such as low fat systems, with long shelf-life are achieved.

Oxygen sensitive systems containing nuts or milk fat that become rancid with time as oxygen migration, and thus lipid oxidation, are reduced by the present invention.

Other products for which the present invention is beneficial are highly flavored snacks of different flavors. At present these need to be packed in different containers or the flavors will be exchanged, thus altering the quality of the product. With the barrier coating of the present invention they can be packed together. For example, products such as chips or other products coated with an inorganic film would form an aroma barrier, making it possible for multi-flavored chips to be packaged within the same container as well.

The Composition of the Inorganic Coating

The coating composition may be any inorganic material. Preferably, the coating material is GRAS certified (Generally Recognized As Safe) by the Food and Drug Administration or can be readily certified as GRAS. More preferably, the coating material forms a barrier against moisture and/or oxygen migration. The preferred coating compounds include $SiO_2$, $SiO$, $CaO$, $ZnO$, $TiO_2$ and $MnO$. $SiO_2$ is desirable in that it is GRAS certified, forms a good barrier and has been used as an ultrathin coating in other fields, such as electronics. $CaO$ is also desirable because of its well known nutritional value. It is particularly preferable to coat $SiO_2$, $MnO$, $CaO$ and $TiO_2$ on surfaces of foods since these compounds are either approved additives, approved dietary supplements, or approved color additives. It is also possible to coat other fortifying minerals on the surface of foods.

The inorganic coating composition is also preferably insoluble or only dispersible in water. "Dispersible" is defined as being the phase of a disperse system consisting of particles or droplets of one substance distributed through another system. This is to insure the resultant films form a lasting effective moisture barrier so that the shelf-life of the product is improved.

The purity of the coating should be controlled in order to insure the resulting edible product is safe. "Purity" is defined as being substantially free from anything that adulterates or taints the edible product. In particular, the term refers to the coating composition being free from contaminates that would affect the safety of the product. Generally the coating composition should be at least 80% pure, preferably at least 90% pure, more preferably at least 95% pure, even more preferably at least 99% pure and most preferably at least 99.9% pure.

$SiO_2$ is particularly advantageous since it is an approved additive ingredient that can be used in food up to 2.0 wt %. Furthermore, $SiO_2$ powders are already commonly used as anti-caking agents. In addition, $SiO$ and $SiO_2$ are currently used in coatings on plastics and glasses to improve oxygen barrier properties. Considered to be retortable and recyclable microwave barriers, glassy materials on plastics were applied to packaging to provide a high oxygen barrier to plastic package films or bottles that were transparent to microwave energy. See, Brody, A. L., "Glass-coated Flexible Films for Packaging: An Overview", *Packaging Technology & Engineering*, February 1994, pages 44–47, hereby incorporated by reference.

The coating compositions of the present invention may comprise a mixture of $SiO$ and $SiO_2$. The coating composition may be given the designation $SiO_x$ because the composition is a mixture, wherein $1 \leq x \leq 2$.

Various compounds utilized as the Si source for chemical vapor deposition (CVD)/chemical plasma deposition (CPD) include organosiliconic esters, anhydrides (often referred to as organosilicates), silane ($SiH_4$), disilane ($Si_2H_6$), and chlorosilanes. Also, included is tetraethoxysilane, ($Si(OC_2H_5)_4$), also known as tetraethylorthosilicate (TEOS). See, Tedder et al., "Mechanistic Studies of Dielectric Thin Film Growth by Low Pressure Chemical Vapor Deposition: The Reaction of tetraethoxysilane with $SiO_2$ Surfaces", *Journal of Applied Physics*, volume 69(10), May 15, 1991, pages 7037–49, hereby incorporated by reference.

Another known precursor for use in plasma deposition includes a mixture of HMDSO (hexomethylene disiloxane), $O_2$ and He.

A low temperature CVD of $SiO_2$ films is disclosed in Desu et al., "Low temperature CVD of $SiO_2$ Films Using Novel Precursors", *J. Electrochem. Soc.*, vol. 139, no. 9, September 1992, hereby incorporated by reference. Novel precursors, hydridospheresiloxanes, namely, $HT8(O_h\text{-}H_8Si_8O_{12})$ and $HT10(D_{5h}\text{-}H_{10}S_{10}O_{15})$, are taught for use in $SiO_2$ deposition in high yields starting from $HSiCl_3$. This procedure results in excellent quality $SiO_2$ thin film deposited on a single crystal silicon substrate. The films are grown at 500° C. and at atmospheric pressure using moist oxygen as a coreactant.

The Coating

The resultant coating should be substantially continuous. "Substantially continuous" is defined as being at least 80% continuous, preferably 90% continuous, more preferably 95% continuous and most preferably 99% continuous. Although cracking, chipping or incomplete application of the coating may reduce the effectiveness of the barrier, such a coating still achieves a reduction in the effects of moisture and/or oxygen migration on the food product. Optimally, however, a continuous coating should be formed as the less continuous the coating, the less effective the barrier mechanism. The inorganic coating should be continuous over at least a significant portion of the edible product and preferably over the entire surface of the edible product. The coating should be thin to reduce the chance of cracking or chipping.

The coatings formed by sputtering and CPD are amorphous, which provides flexibility to further prevent cracking or chipping. The flexible character of the coatings can be increased by adding additives during the coating process.

The thickness of the coating is also an important consideration. The thickness of the coating is proportional to the weight percentage of coating composition with respect to the weight of the edible product. It is often preferred or required to maintain the content of the coating composition to a minimum because of safety concerns or regulatory requirements. In addition, the thickness of the coating is also important since it can affect the character of the edible product, including the product's taste, texture and smell. Also, the thickness of the coating ultimately determines the effectiveness of the film as a barrier.

Since the mouth can detect particle sizes of 20 microns or greater as gritty or chalky the inorganic coating should have a thickness of less than about 0.5 microns. Preferably, the inorganic film should have a thickness of about 0.0001 to 0.2 microns, more preferably about 0.0001 to 0.1 microns, even more preferably about 0.0002 to 0.05, and most preferably about 0.0005 to 0.02 microns.

The inorganic coating should also be substantially uniform in both its thickness and composition. "Substantially uniform" is defined as being that uniformity necessary to result in a product having the desired properties, preferably with less than a 100% variation, more preferably less than 50% variation, even more preferably less than 25% variation, and most preferably less than 10% variation.

The amount of coating used to cover the edible product is to be controlled so that the resultant product is safe. This will depend on the edible product and the coating materials used. Generally, the amount of coating composition in the resultant edible product should be less than about 0.05 wt %, preferably less than about 0.01 wt %, more preferably less than about 0.005 wt %, even more preferably less than 0.001–0.002 wt %, most preferably less than about 0.0005 wt %.

Additional objects, advantages and features of the various aspects of the present invention will become apparent from the following description of its preferred embodiments, such description being given in conjunction with the accompanying drawings.

DESCRIPTION OF THE PREFERRED EMBODIMENTS

Figure 1:
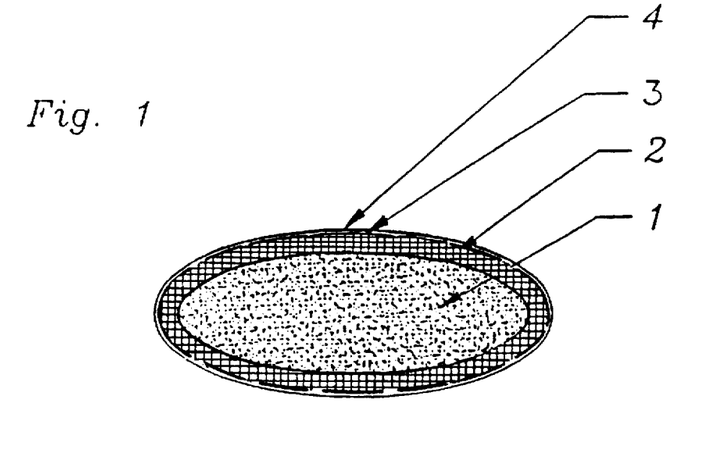
FIG. 1 illustrates an elevational view in section of a portion of an elliptical edible product covered by a sugar coating, a polish and finally an edible inorganic coating.

Referring initially to FIG. 1, an edible product is illustrated that includes an elliptical chocolate product 1 coated with a first sugar coating to form a sugar shell 2, further coated with a polish 3, and finally coated with an inorganic coating 4.

Figure 2:
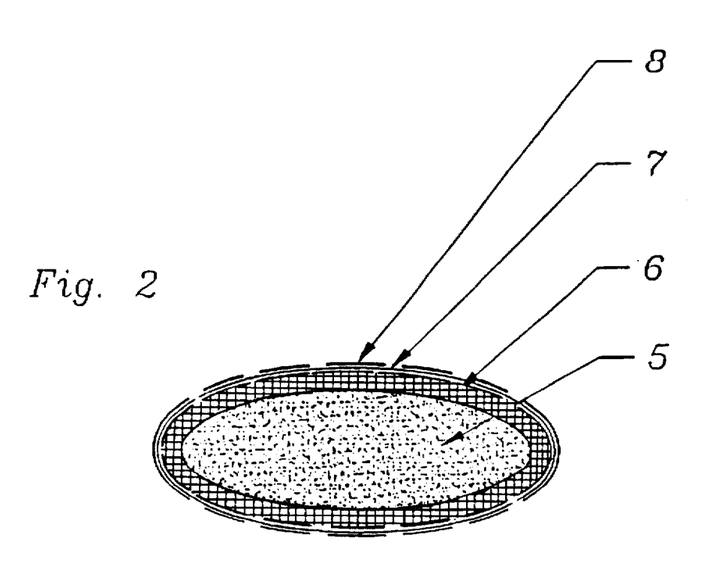
FIG. 2 illustrates an elevational view in section of a portion of an elliptical edible product having a first sugar shell, then an inorganic edible precoating and then covered by a polish coating.

FIG. 2 illustrates an elliptical chocolate product 5 coated with a sugar shell 6, further coated with an inorganic coating 7 and finally coated with a polish 8.

Figure 3:
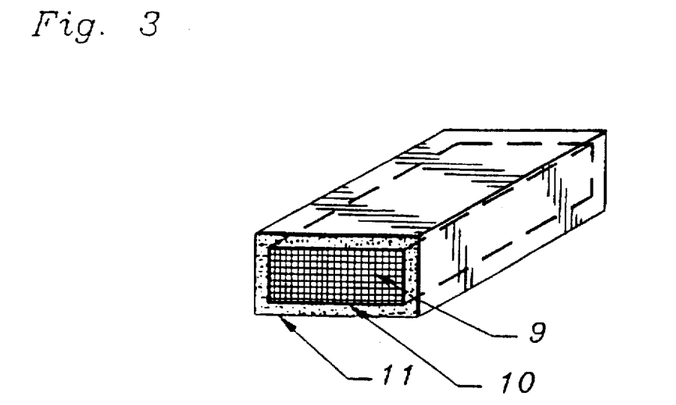
FIG. 3 illustrates a perspective view partly in section of an edible bar product in accordance with a preferred embodiment of the present invention an edible bar product coated with an edible inorganic coating and then covered with a second coating.

FIG. 3 illustrates an edible product comprising a center of confection components 9 coated with an inorganic coating 10, and finally enrobed in a chocolate coat 11.

Figure 4:
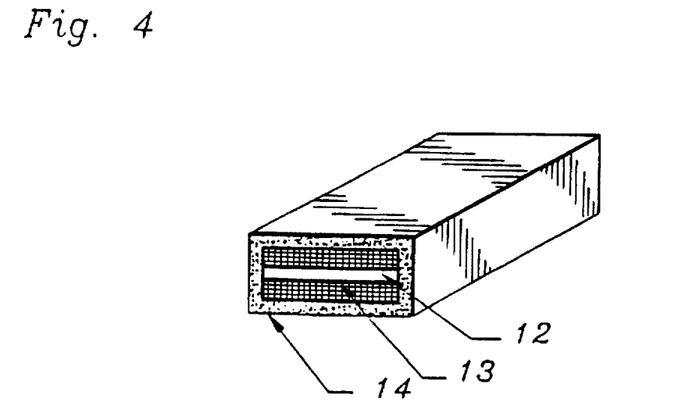
FIG. 4 illustrates a perspective view partly in section of an edible bar product in accordance with a preferred embodiment of the present invention of an edible bar product precoated with an edible inorganic coating and then covered by a second edible coating.

FIG. 4 illustrates an edible product comprising a center of confection components 12 coated with an inorganic coating 13 and finally enrobed in a chocolate coating 14.

Figure 5:
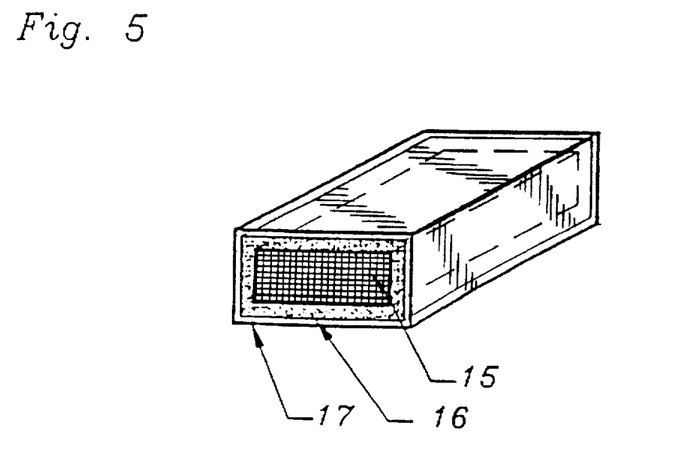
FIG. 5 illustrates a perspective view partly in section of an edible bar product in accordance with a preferred embodiment of the present invention of an edible bar product coated with an edible inorganic coating.

FIG. 5 illustrates an edible product comprising a center of confection components 15 coated with a chocolate coating 16, and finally coated with an inorganic coating 17.

Figure 6:
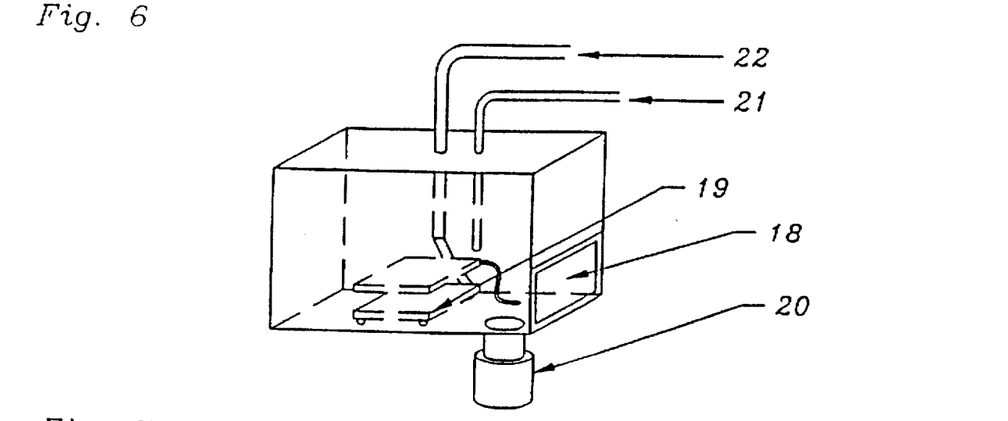
FIG. 6 is a schematic flow diagram for a batch apparatus used for coating edible products with an edible film.

FIG. 6 illustrates a batch sputtering process where the food to be coated is placed in an enclosed plasma deposition apparatus 17 in plasma deposition area 19. After door 18 is closed, a vacuum is pulled by pump 20, and the enclosed area is back flushed with an inert or reacting gas through supply line 21 and brought up to processing vacuum. An electrical current from a suitable power source (not shown) is supplied through electrodes 22 to create the plasma. After adequate time for coating the product, electrical current and pump 20 are shut off and gas 21 exhausted to permit door 19 to be opened and the coated product removed.

Figure 7:
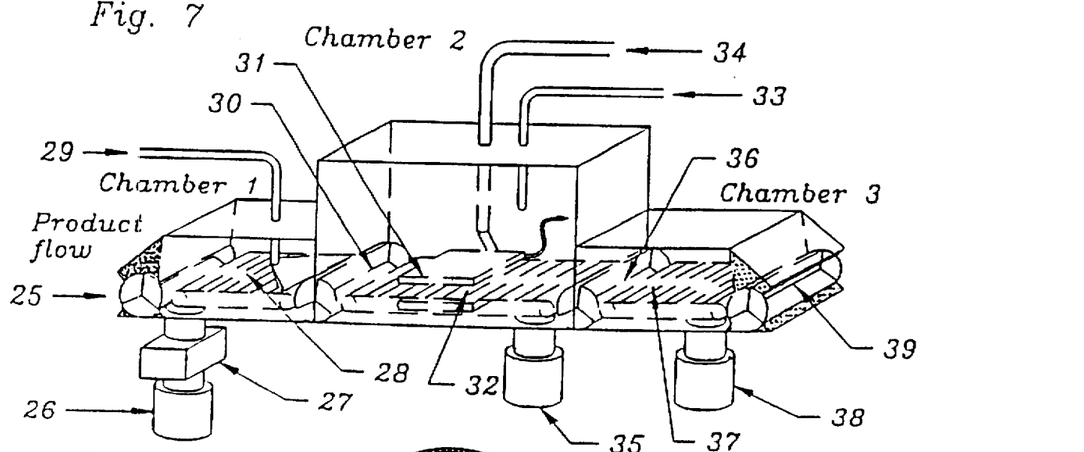
FIG. 7 is a schematic flow diagram for a continuous apparatus used for coating edible products with an edible film.

FIG. 7 illustrates a continuous system for a plasma depositor. In the continuous process for plasma deposition three separate enclosed chambers 1, 2 and 3 are used with each chamber being under separate vacuum control. Product enters chamber 1 on conveyor belt 28 through a star valve 25 which precludes entry of outside air. A vacuum is maintained in chamber 1 by pump 26 through valve 27 and an inert or reactive gas through supply line 29 flushes the product. Conveyor belt 28 moves the product through star valve 30 into chamber 2. Star valve 30 isolates chamber 1 from chamber 2. After passing through star valve 30 the product is deposited on conveyor belt 31 to plasma depositing area 32. Plasma is created by electrical current from a power source (not shown) supplied through line 33 to electrodes 34 in the presence of the inert or reactive gas and vacuum is maintained by pump 35. The plasma coats the product. The coated product then passes through star valve 36 to chamber 3 on conveyor belt 37. A vacuum less than that in chamber 2 is maintained in chamber 3 by pump 38. The product then exits chamber 3 through star valve 39 and onto a conveyer belt to the conventional food processing line.

Figure 8:
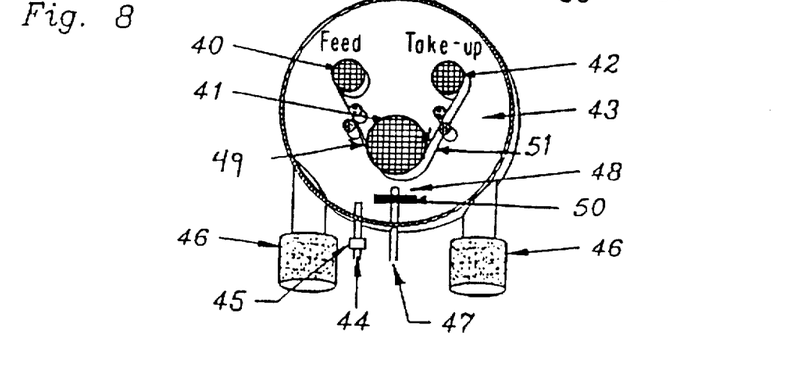
FIG. 8 is a schematic flow diagram for a batch apparatus to produce an edible film on a films product.

FIG. 8 illustrates a sputtering depositor that coats a sheet of edible inorganic film onto a flexible sheet 49. The edible coating can be subsequently separated from the flexible sheet 49 and incorporated into products such as those shown in FIG. 4. A pre-made flexible sheet 49 is placed in a chamber 43. The flexible sheet is unrolled from feed drum 40 over a chill roll 41. The inorganic target 48 is placed on a plate 50 and sputtered onto flexible sheet 49 by applying electrical energy through supply 47 in the presence of gas obtained from gas supply 44 regulated by a valve 45. The coated flexible sheet 51 is then taken up by take-up drum 42. The vacuum, power, and gases are shut off before the product is removed. The process is somewhat similar to the deposition system of FIG. 6, as a vacuum is pulled in chamber 43 first to remove air by one or more pumps 46 and reacting and/or inert gases are introduced into the chamber for the deposition process. However, unlike CPD, where the gas is ionized and the charged ions attracted to the product, in sputtering, charge particles are accelerated into the target which results in particles from the target being ejected onto the substrate, here flexible sheet 49. The resultant pre-made sheet of inorganic material may be stored, separated from the flexible sheet and applied onto an edible product as a barrier.

EXAMPLES

Experiments have been completed using both Sputtering and Chemical Plasma Depositions (CPD) techniques. In both cases, the outer polish coating used on certain products appear to cause the $SiO_2$ to produce dusty patches on the coated product. Also, it was discovered that a certain operating wattage range (about 50 watts) was preferable for products with low melting temperatures, such as chocolate products (melting temperature about 20° C.).

Sputtering is a more severe vacuum process than CPD. Also, CPD places an estimated 1000 angstrom layer on the product about 10× times faster then sputtering. CPD produced a coating comparable to that produced by sputtering, but at only 50 Watts.

Example 1

The edible product used was SKITTLES® Bite Size Candies. Theses are a sugar coated fruit flavored toffee candy. In the manufacture of SKITTLES® Bite Size Candies, sugar is mixed with the flavor to form the toffee. The toffee is then formed into an elliptical center. The center is then coated with a sugar solution and air dried. The product is polished and finally printed with the letter S. SKITTLES® heretofore have exhibited adverse effects when exposed to excessive moisture for long periods.

The SKITTLES® product was placed into a reaction chamber of a laboratory apparatus of the type shown in FIG. 6 and the door of the chamber closed. A vacuum was then pulled to a base pressure of 50–200 mtorr. The chamber was flushed with Argon at 45 sccm and then by oxygen at 8 sccm until the chamber was full of pure oxygen. The TEOS (tetraethylorthosilicate) tube was heated to 95° C. to vaporize the TEOS before entering the chamber. The power was turned on to about 50 watts and fed through an RF coupling device that was set at 13.56 MHZ. The plasma was started and the TEOS valve was turned on to allow the TEOS to react with the oxygen in the plasma and coat the SKITTLES® Bite Size Candies. After 10 minutes the power, the oxygen and TEOS gases and lastly the vacuum pump was shut off. The chamber was opened and product was removed.

Preferably the electrical power should be supplied to the bottom plate and the product set on this bottom or "hot" plate. Alternatively, the power may be supplied directly to the edible product if it is conductive. This procedure allows the $SiO_2$ to directly coat the surface with reduced dusting. This is due to the positive nature of SiO+ from the TEOS. In any case, the process resulted in the reduced dusting of the $SiO_2$ on the surface that was formed in the plasma and coated the product. Thus, the $SiO_2$ was placed on the product without dusting.

Conditions:

|  | Range | Ideal |
| --- | --- | --- |
| Electrode Separation | 1–3 inches | (1.5) |
| Electrode Area | 15–50.0 inches | (32.0) |
| Argon Flow | 25–100 sscm | (45 sscm) |
| Oxygen Flow | 1–20 sscm | (8 sscm) |
| TEOS temperature | 85–110° C. | (95° C.) |
| RF (13.56 MHZ) | 25–100 watts | (50 watts) |
| Deposition time | 5–25 minutes | (15 mins) |
| Base pressure | 50–500 mtorr | (200 mtorr) |

The coated SKITTLES® were tested by evaluating the effects of exposure to moisture. An uncoated SKITTLES® was placed in a vial of water and began dissolving immediately. A SKITTLES® coated with the inorganic film was placed in a vial of water and did not begin to dissolve until after 4 minutes. It is believed that this time can be still further increased if 'pin holes' present in the coating are reduced or eliminated and a more even inorganic coating is placed on the product. It is envisioned that with a more carefully constructed apparatus the number and size of 'pinholes' will be reduced.

Example 2

In this example, TWIX® Caramel Cookie Bars are used. Twix® Bars are cookies that are topped with a caramel coating then enrobed with chocolate. This type of product is illustrated in FIG. 4. The shelf-life is somewhat limited due to water migration from the caramel to the cookie. This water migration softens the cookie and with age a poorer quality product than initially manufactured results. In this example, the preprocess apparatus is installed before an apparatus as illustrated in FIG. 7 to produce a cookie cut into bar lengths. Then the product is passed through the star valve 25 which is designed to allow for the insertion of the product into a chamber 1 where a vacuum was pulled to 20 torr without dropping the vacuum level. The product then passes through star valve 30 to chamber 2 where the plasma coats the product with the inorganic layer. After coating the product passes through star valve 36, into chamber 3 which is maintained at a vacuum of 30 torr. After passing through star valve 39 the product exits having been coated with an inorganic film. The product then continues on the conventional confectionery line for further processing. The barrier on the cookie reduces the migration of moisture and oxygen to and from the cookie, thereby increasing the shelf-life of the product.

Example 3

This example uses "M&M's"® Chocolate Candies which are elliptically shaped chocolate centers coated with a sucrose solution containing coloring to form a candied coating. The color coating on the "M&M's"® Chocolate Candies eventually rubs off in time when exposed to humid conditions. To increase the quality of the confection a moisture barrier according to the present invention is desirable. In this example a batch process which entails placing a perforated bed rotating pan ("perforated tumbler") inside a plasma reactor similar to FIG. 7, is employed. The product is placed into a tumbler which is then placed into chamber 1 and then a vacuum is pulled to 0.1 torr. The tumbler is then back flushed with $O_2$ to a vacuum of 10 torr. The tumbler is then set into motion into chamber 2 and the plasma starts to coat the product. After coating, the chamber is pressurized and product removed from the tumbler. The inorganic coating on the chocolate candies improves the shelf-life and quality of the product by reducing the deleterious effects of exposure to moisture.

Example 4

In this example, coated chocolate chips or coated "M&M"'s® Chocolate Candies or "M&M's"® Milk Chocolate Baking Bits are used. These types of candies generally bleed their color into food products, such as cookie or ice cream products when they are added to such products. This produces a "halo" or color ring within the product that in some cases is not aesthetically appealing. Products and/or their ingredients are coated similar to EXAMPLE 2 (see FIGS. 1 and 2) to reduce this discoloring. The coated products are incorporated into cookie or ice cream products without the resultant "halo formation".

Example 5

Coated "ready to eat" cereals become soggy in milk soon after the milk is added to the cereal. By the time the consumer finishes the bowl, the cereal is generally soggy. With the exception of sugar coated cereals, this attribute lowers the eating appeal of the food product. It is possible to reduce moisture migration with the technology of the present invention by coating the cereal with an inorganic coating, without the need to add extra sugar. Because cereals are already fortified, this coating will add to the mineral and nutritional claim if the inorganic film contains nutrients. A process to coat cereals may be performed using the apparatuses shown in FIGS. 6 and 7. The barrier formed on the cereal will be optimized so that the product does not become soggy when mixed with milk. Since the cereal product is only exposed to milk for a relatively short period of time (1–10 minutes), the coating thickness can accordingly be adjusted. If an oxygen/moisture barrier coating is used the resultant product will also have a longer shelf-life due to decreased oxygen migration. The product will therefore be less likely to become stale.

As illustrated by the foregoing description and examples, the present invention has great application for the formulation of a wide variety of edible products. The present invention provides for edible products having extended shelf-life and uses without detrimentally affecting the taste, texture and smell of the product. The present invention allows for the reduction of the cost of packaging without reducing the shelf-life of the product as less expensive packaging may be used instead of more costly foil or barrier packaging materials. This is a further environmental benefit in that such expensive packaging material are not readily biodegradable.

The terms and expressions which have been employed are used as terms of description and not of limitations, and there is no intention in the use of such terms or expressions of excluding any equivalents of the features shown and described as portions thereof, its being recognized that various modifications are possible within the scope of the invention.

We claim:

1. A coated edible product comprising:
   a. an edible material; and
   b. a substantially continuous inorganic coating on a surface of the edible material, wherein said coating covers at least a portion of the edible material and said coating has a thickness ranging from 0.0001 to 0.5 microns.

2. The coated edible product of claim 1, wherein the inorganic coating forms a barrier that reduces the migration of moisture, oxygen or mixtures thereof.

3. The coated edible product of claim 1, wherein the inorganic coating has a thickness of 0.0002 to 0.2 microns.

4. The coated edible product of claim 3, wherein the inorganic coating has a thickness of 0.0002 to 0.1 microns.

5. The coated edible product of claim 4, wherein the inorganic coating has a thickness of 0.0002 to 0.05 microns.

6. The coated edible product of claim 1, wherein the inorganic coating forms a substantially continuous layer on the entire surface area of the edible material.

7. The coated edible product of claim 1, wherein the inorganic coat is at least 95% continuous.

8. The coated edible product of claim 1, wherein the inorganic coating comprises at least one compound selected from the group consisting of $SiO_2$, SiO, CaO, ZnO, $TiO_2$ and MnO.

9. The coated edible product of claim 1, wherein the inorganic coating consists essentially of $SiO_2$, SiO, CaO, ZnO, $TiO_2$ or MnO.

10. The coated edible product of claim 1, wherein the inorganic coating consists essentially of a mixture of SiO and $SiO_2$.

11. The coated edible product of claim 1, wherein the inorganic coating is substantially pure.

12. The coated edible product of claim 1, further comprising a precoating material which is applied onto the edible material before the inorganic coating.

13. The coated edible product of claim 1, wherein the edible material is a water-containing filling and the inorganic coating separates the water-containing filling from an edible outer portion.

14. The coated edible product of claim 1, wherein the coated edible product comprises more than one inorganic coating.

15. The coated edible product of claim 1, wherein the inorganic coating is 0.0001 to 0.05 wt % of the coated edible product.

16. The coated edible product of claim 1, wherein the edible material is substantially solid.

17. The coated edible product of claim 1, wherein the edible material is a gel.

18. A coated edible product comprising:
   a. an edible material; and
   b. an inorganic coating applied onto an outer surface of the edible material, wherein the coating is a substantially uniform film having less than 50% variation in thickness and a thickness ranging from 0.0001 to 0.5 microns.

19. The coated edible product as claimed in claim 18, wherein said uniform film has less than 25% variation in thickness.

20. The coated edible product of claim 18, wherein the inorganic coating comprises at least one compound selected from the group consisting of $SiO_2$, SiO, CaO, ZnO, $TiO_2$ and MnO.

21. The coated edible product of claim 18, wherein the inorganic coating consists essentially of a mixture of SiO and $SiO_2$.

22. The coated edible product of claim 18, wherein the inorganic coating is at least 95% pure.

23. The coated edible product of claim 18, wherein the inorganic coating is 0.0001 to 0.05 wt % of the coated edible product.

24. The coated edible product of claim 18, wherein said coating is formed atom by atom to form the uniform film.

25. A coated edible product comprising:
   a. an edible material; and
   b. an inorganic coating applied onto an outer surface of the edible material, wherein the coating is less than 0.05 wt. % of the coated edible product.

26. The coated edible product of claim 25, wherein the inorganic coating has a thickness ranging from 0.0001 to 0.5 microns.

27. The coated edible product of claim 25, wherein the inorganic coating comprises at least one compound selected from the group consisting of $SiO_2$, SiO, CaO, ZnO, $TiO_2$ and MnO.

28. The coated edible product of claim 25, wherein the inorganic coating consists essentially of a mixture of SiO and $SiO_2$.

29. A method of producing the edible product of claim 1, which method comprises coating the edible product by plasma deposition or sputtering with a substantially continuous coating of inorganic material that covers at least a portion of the edible product.

* * * * *

UNITED STATES PATENT AND TRADEMARK OFFICE
CERTIFICATE OF CORRECTION

PATENT NO. : 5,741,505

DATED : April 21, 1998

INVENTOR(S) : DANIEL L. BEYER, ET AL.     Page 1 of 2

It is certified that error appears in the above-identified patent and that said Letters Patent is hereby corrected as shown below:

COLUMN 2

Line 48, "disperseable" should read --dispersible--.

COLUMN 4

Line 34, "effecting" should read --affecting--;
    Line 42, "effecting" should read --affecting--; and
    Line 66, "effect" should read --affect--.

COLUMN 8

Line 37, "contaminates" should read --contaminants--.

COLUMN 9

Line 6, "hexomethylene" should read --hexamethylene--.

COLUMN 10

Line 24, "an" should read --of an--.

COLUMN 12

Line 1, "10X" should read --10--;
    Line 3, "Watts" should read --watts--;
    Line 6, "Theses" should read --These--;
    Line 18, "Argon" should read --argon--;
    Line 23, "MHZ" should read --MHz--;
    Line 28, "was" should read --were--;
    Line 49, "MHZ" should read --MHz--; and
    Line 59, " 'pin holes' " should read --'pinholes'--.

UNITED STATES PATENT AND TRADEMARK OFFICE
CERTIFICATE OF CORRECTION

PATENT NO. : 5,741,505

DATED : April 21, 1998

INVENTOR(S) : DANIEL L. BEYER, ET AL.    Page 2 of 2

It is certified that error appears in the above-identified patent and that said Letters Patent is hereby corrected as shown below:

<u>COLUMN 14</u>

Line 21, "material" should read --materials--; and
Line 27, "its" should read --it--.

Signed and Sealed this

Twenty-fourth Day of November,1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,741,505

DATED : April 21, 1998

INVENTOR(S): DANIEL L. BEYER ET AL.

It is certified that error appears in the above-identified patent and that said Letters Patent is hereby corrected as shown below:

<u>COLUMN 12</u>

Lines 45-50, "sscm" (all occurrences) should read --sccm--.

Signed and Sealed this

Fifteenth Day of June, 1999

*Attest:*

Q. TODD DICKINSON

*Attesting Officer*   Acting Commissioner of Patents and Trademarks